United States Patent
Shah et al.

[11] Patent Number: 4,824,677
[45] Date of Patent: Apr. 25, 1989

[54] GROOVED TABLET FOR FRACTIONAL DOSING OF SUSTAINED RELEASE MEDICATION

[75] Inventors: Ashok C. Shah, Portage; Nancy J. Britten, Kalamazoo; Joseph N. Badalamenti, Portage, all of Mich.

[73] Assignee: The Unjohn Company, Kalamazoo, Mich.

[21] Appl. No.: 943,979

[22] Filed: Dec. 18, 1986

[51] Int. Cl.$^4$ .............................................. A61K 9/44
[52] U.S. Cl. ..................................... 424/467; D16/3; D1/12; 424/473
[58] Field of Search ............................... 424/464–473, 424/408; D16/3; D1/12

[56] References Cited

U.S. PATENT DOCUMENTS

| | | | |
|---|---|---|---|
| D. 89,941 | 5/1933 | Low | 424/467 X |
| 2,312,381 | 3/1943 | Bichenhauser | 424/467 |
| 3,336,200 | 8/1967 | Krause et al. | 424/467 X |

FOREIGN PATENT DOCUMENTS 1246508 9/1971 United Kingdom .

Primary Examiner—Nancy A. B. Swisher
Attorney, Agent, or Firm—Flynn, Thiel, Boutell & Tanis

[57] ABSTRACT

A divisible matrix table structure with or without coating, having controlled and delayed release of the active substance, and having first and second body parts, each having top and bottom facing surfaces joined together at a perimeter of an edge means. A breakable connecting structure is provided for joining together the first and second body parts. The breakable connecting structure is formed by depressions in the top and bottom facing surfaces of the first and second body parts. Each of the depressions is directly opposite the other and have first and second score surfaces facing each other.

28 Claims, 3 Drawing Sheets

GROOVED TABLET FOR FRACTIONAL DOSING OF SUSTAINED RELEASE MEDICATION

FIELD OF THE INVENTION

This invention relates to divisible tablets for facilitating fractional dosing of medication which retain their sustained release property after division into discrete segments. The designs of the present invention minimize the amount of new surface area created upon division, thus making possible the preparation of divisible sustained release matrix tablets.

Basic design features include: 1. laterally extending grooves on the top and bottom tablet surfaces at each line of division which may be of variable depth, and 2. a tablet shape which provides deep laterally opening grooves on the sides of the tablet in the same plane as the top and bottom laterally extending grooves. Designs described in the present invention minimize the formation of new surface upon division and thereby provide means of administrating a fraction of the sustained release dose without substantially altering its rate of drug release.

BACKGROUND OF THE INVENTION

A number of multiple dose divisible tablet designs have been reported, most of them for the conventional fast release tablets with the laterally extending grooves. Derwent abstract 35867W/21; 13237: 70026V/40; 18289; 19988; 37707; and 20761U-B give examples of such divisible fast release tablets. None of these designs specify the relationship between laterally opening side grooves and laterally extending top and bottom grooves as described in the present invention, nor do they refer to the sustained release dosage forms.

Tablets having laterally extending grooves on the top and bottom surfaces and a small laterally opening groove on the sides are described in Derwent abstracts 71600C/41 and 5873C/33. However, these grooves are provided to facilitate ease in breaking the tablet, and not for the purpose of prescribing sustained release dosage forms. Since division of these tablets exposes a substantial amount of new surface, these tablets will not be suitable for sustained release preparations.

A controlled release theophylline tablet with laterally extending grooves on the flat tablet surfaces is described in Derwent abstract 85413D/47. Here again, substantial new surface is produced upon division of the tablet. No mention has been made of the laterally opening grooves to minimize the exposed surface as in the present invention.

Derwent abstract 28075 mentions a sustained release divisible tablet using a V-shaped center core and layering of the active ingredient. This design also would result in the exposure of appreciable new surface upon tablet division and thus, change in the drug release rate.

The controlled release divisible tablet designs described in the U.S. Pat. No. 4,353,887 come closest to achieving comparable drug release rates for the whole tablet and its fragments. However, as with the other above described designs, here also, tablet division produces relatively large new surface. To control the rate of release, the drug must be arranged in longitudinal layers within the tablet, which precludes its application to simple matrix tablets as in the present invention.

Although the above mentioned patents describe a variety of divisible tablet forms for sustained (controlled) release preparations, none attempt to effectively minimize the amount of new surface area exposed after division. None of them refer to having laterally opening side grooves along with the laterally extending grooves on the faces of the tablet in order to minimize the exposed new surface upon division of the tablet. Laterally opening and laterally extending grooves described in the present invention significantly reduce the exposure of new surface upon tablet division and, therefore, the fragments will retain the release rate of the whole tablet.

The major objective of the invention is to provide divisible tablets that will retain their sustained release property when divided into two or more discrete segments. The unique designs described in the present invention provide partial dose fragments with a minimum of exposed new surface created after the division of the whole tablet. As a result, the sustained release characteristics of the whole tablet are retained by each segment of the tablet.

SUMMARY OF THE INVENTION

Design features presented in the present invention can be applied to the preparation of sustained release tablets which are divisible into a number of discrete segments e.g. 2, 3, 4, 5, 6, etc. The shape of the individual segments and whole tablet, as well as the depth and angle of the dividing grooves may be varied depending on the number of divisions desired per tablet; tablet size, weight, strength and other formulation considerations.

The advantages of the present invention over the conventional sustained release matrix tablets are substantial. With the conventional sustained release matrix tablets the increase in the exposed new surface upon division leads to significant change in the release rate as compared to the whole tablet. In instances where the rate of release is partially or totally controlled by a coating, conventional tablet designs create a fragment where a fairly large portion of the coating has been broken away, thus exposing the unprotected surface which dissolves at a more or less uncontrolled rate.

Designs of four multiple dose sustained release divisible tablets are illustrated. The basic design features covered by the present invention include: 1. laterally extending grooves on the top and bottom tablet surfaces at each line of division, and 2. a tablet shape which produces deep laterally opening grooves on the sides of the tablet that are in the same plane as the laterally extending grooves.

DETAILED DESCRIPTION

For purposes of the discussion present in this disclosure, the phrase "lateral" direction will have reference to a direction that extends outwardly from the geometric center of the tablet toward a peripheral edge of the tablet via the shortest distance. A "laterally" opening groove will have reference to a notch or groove in the peripheral edge of the tablet that faces laterally outwardly from the tablet.

Figure 1:
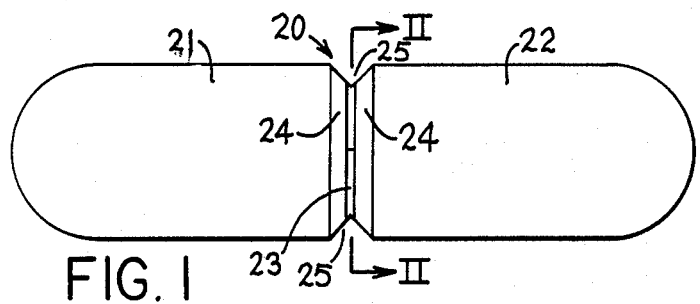
FIG. 1 illustrates a top view of a divisible tablet embodying the present invention.
Figure 5:
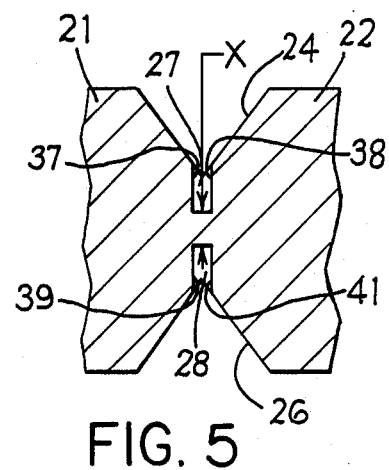
FIG. 5 is a sectional view taken along the line V—V of FIG. 4.

FIG. 1 illustrates a tablet 20 embodying the invention and which includes a pair of tablet sections 21 and 22 joined together at a common laterally extending edge structure 23. The area adjacent to the common edge structure 23 is bevelled as at 24 on the upper side of the tablet as at 26 (FIGS. 3 and 5) on the underside of the tablet. The lateral edges of the tablet 20 are provided with laterally opening notches 25 to reduce the lateral width dimension of each tablet section 21 and 22 at the common edge 23. Thus, the width dimension of the common edge 23 measured along a line parallel to the common edge 23 is less than the maximum width of the tablet sections 21 and 22.

Figures 2, 3:
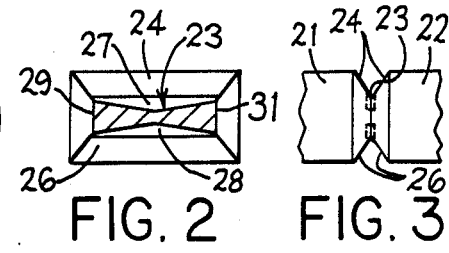
FIG. 2 is a sectional view taken along the line II—II of FIG. 1.
FIG. 3 is a side view of the embodiment illustrated in FIG. 1.
Figure 4:
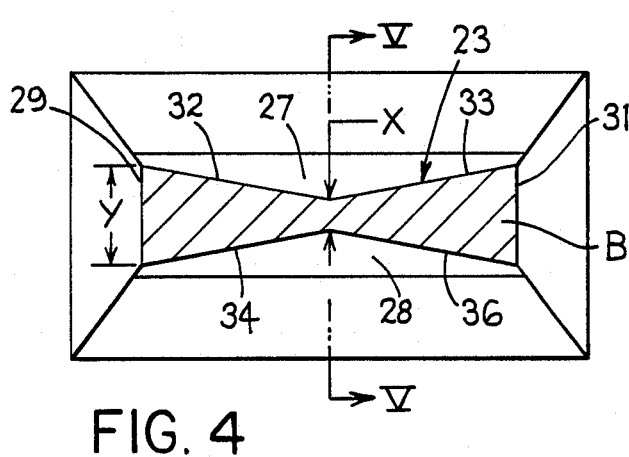
FIG. 4 is an enlarged version of FIG. 2.

Referring now in more detail to the common edge structure 23, it is to be noted that there is a depression 27 provided on the top surface of the tablet and a further depression 28 provided on the bottom surface of the tablet as illustrated in FIGS. 2 and 4 and vertically aligned with the depression 27. The depression is most shallow at the lateral edges 29 and 31 of the common edge 23 and is the deepest at the geometric center of the common edge 23. In this particular embodiment, the cross-sectional shape for each depression 27 and 28 is a triangular shape, preferably an isosceles triangle, wherein the edge surfaces 32 and 33 of the upper triangular shaped depression 27 are equal and wherein the edges 34 and 36 of the lower depression 28 are equal. The ratio of the thickness of the cross-sectional area B of the common edge 23 at the juncture between the straight edge surfaces 32, 33 and 34, 36, namely, the thickness "X", is preferably in the range of ⅛ to ⅓ the thickness of the lateral edges 29 and 31, whose dimension is represented by the character "Y" in FIG. 4.

Figure 6:
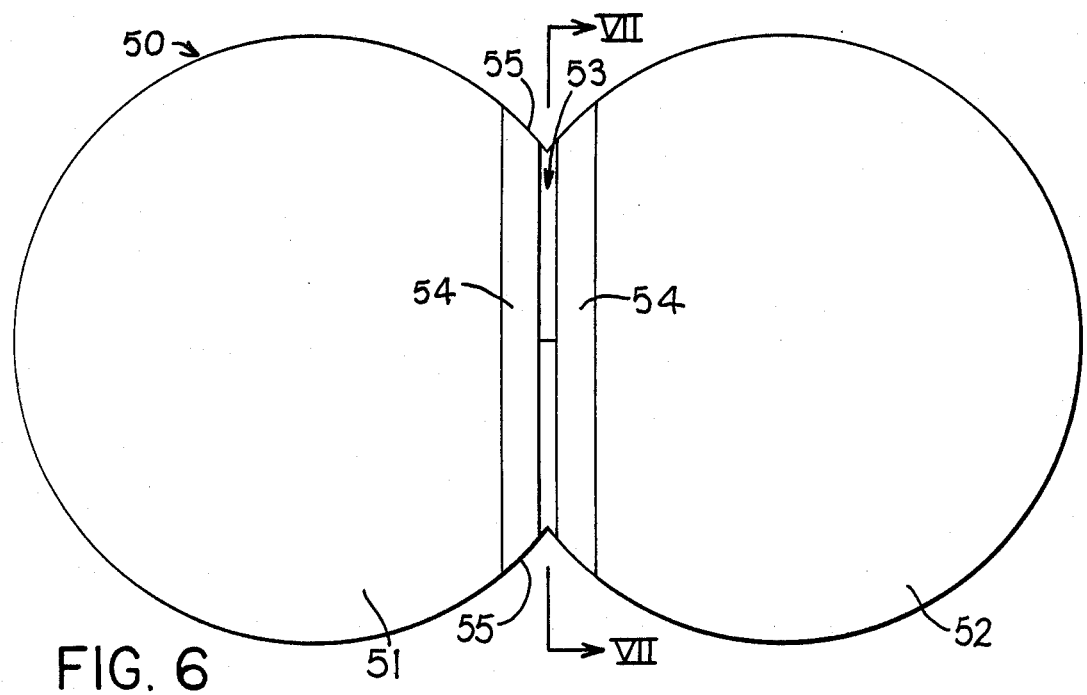
FIG. 6 is a top view of a divisible tablet having a different shape and embodying the invention.
Figure 7:
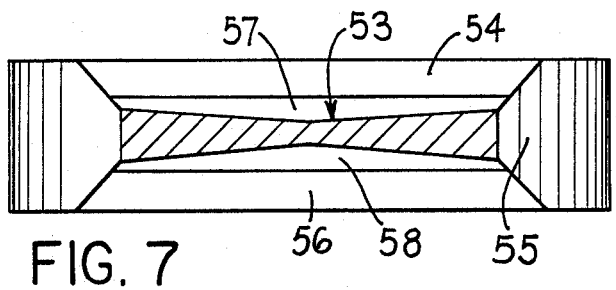
FIG. 7 is a sectional view taken along the line VII—VII of FIG. 6.

FIGS. 6 and 7 illustrate a further embodiment of a tablet 50 having a pair of circular shaped tablet sections 51 and 52. The two tablets sections 51 and 52 are connected by a common edge structure 53. The mutually adjacent edges of each of the tablet sections 51 and 52 are bevelled or chamfered as at 54 on the upper side of the tablets sections 51 and 52 and as at 56 on the underside of each tablet section. The tablet 50 has a pair of laterally facing notches 55 at the opposite lateral ends of the common edge 53 so that the width dimension of the common edge 53, when measured along a line parallel to the common edge 53 is less than the maximum width of the tablet sections 51 and 52. The common edge 53 has a construction nearly identical to the construction of the common edge 23 illustrated in the embodiment of FIGS. 1 to 5. That is, the common edge has a pair of depressions 57 and 58 on the upper and lower surfaces thereof, which depressions are vertically aligned and have a depth which is the greatest at the geometric center of the common edge 53 and tapering to a minimum depth at the ends of the common edge. The characteristics of the surfaces within the depression are identical to the characteristics illustrated in FIGS. 1 to 5. In the embodiment of FIGS. 6 and 7, following a separation of an experimental divisible tablet into its two tablets sections, each of the divided segments had only an increase in surface area of about 2.2%.

Figure 8:
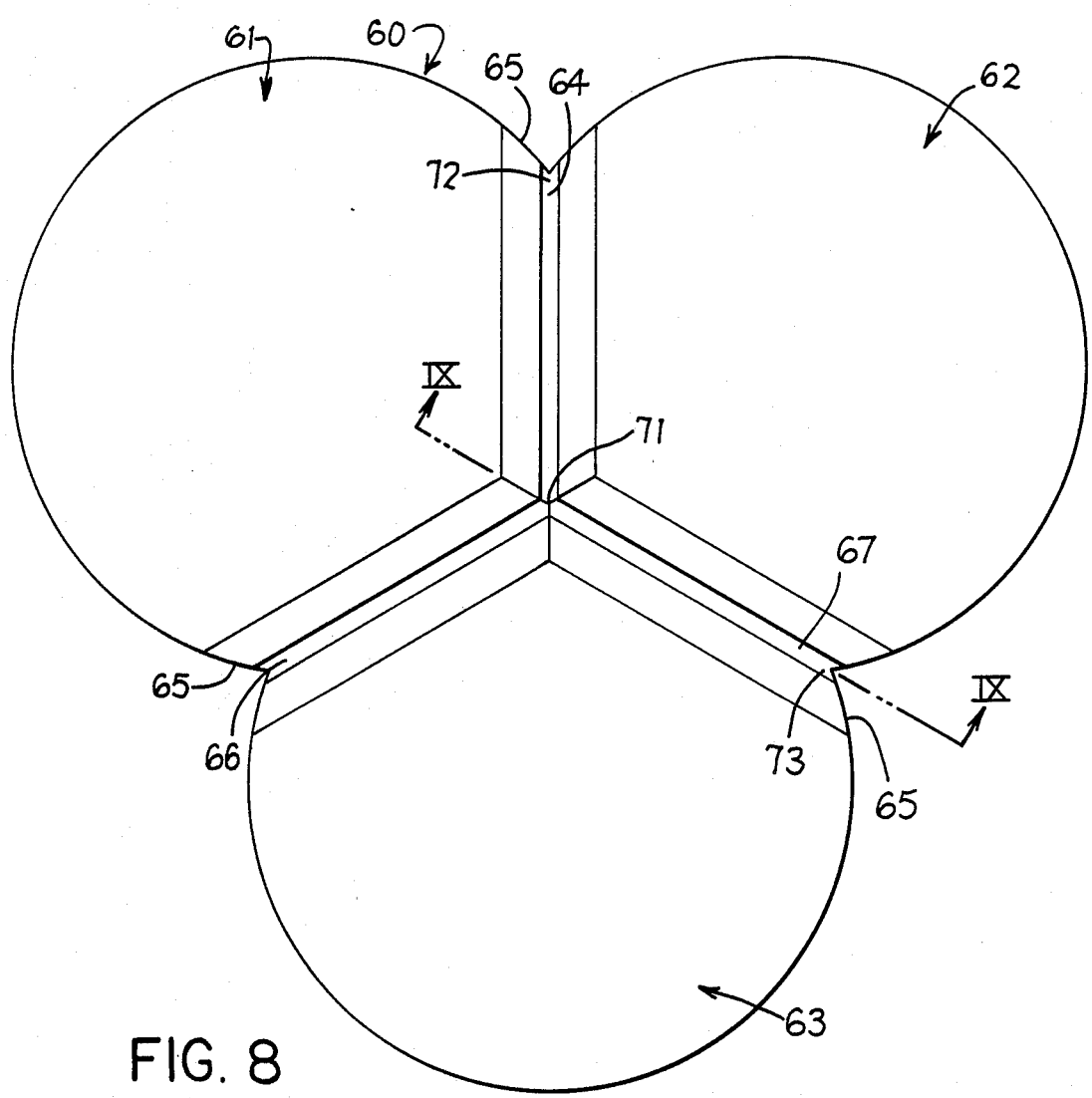
FIG. 8 is a top view of a divisible tablet having a still further different shape.
Figure 9:
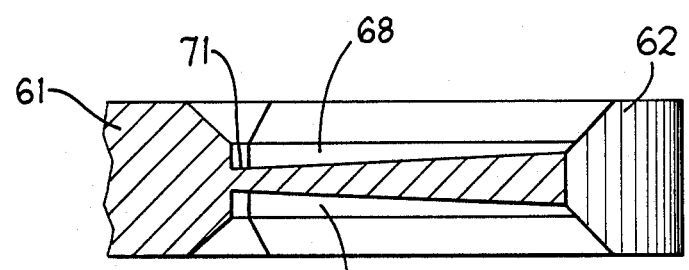
FIG. 9 is a sectional view taken along the line IX—IX of FIG. 8.

The divisible tablets illustrated in FIGS. 1 to 7 are also known as bidosage divisible tablets. A tri-dosage tablet 60 is shown in FIGS. 8 and 9. Tablet 60 has, as its name implies, three tablet sections 61, 62 and 63. Each tablet section 61, 62 and 63 has an edge that is common to the remaining two sections. For example, tablet sections 61 and 62 have a common edge 64. The tablet sections 61 and 63 have a common edge 66. The sections 62 and 63 have a common edge 67. The tablet 60 has three laterally opening notches or grooves 65 around the periphery so that the length of each common edge 64, 66 and 67 is minimized. As in the other embodiments, the common edges 64, 66 and 67 are each defined by a pair of vertically aligned depressions 68 and 69, FIG. 9 being representative of the three depressions. The depth of each depression 68 and 69 is the greatest at the geometric center of the common edges tapering to a minimum depth at the outer ends of the common edges. Although the common edges 63 and 67, 64 and 66, and 66 and 67 are angled with respect to each other, namely, at a 120 degree angle, the cross-sectional shape of the area exposed following a severing of the tablet 60 into its individual tablets sections 61, 62 and 63 is the same as that illustrated in FIG. 9. That is, starting at the outer edge of the common edge 64 and traversing the common edge to the outer edge of the common edge 67, the depth of the depressions 68 and 69 are the greatest at the geometric center 71 of the common edges tapering to a minimum depth at the outer ends as at 72 and 73. The characteristics of the sidewalls of the depressions 68 and 69 are the same as the characteristics present in the embodiment of FIGS. 1 to 5. Thus, further description concerning the depression 68 and 69 are believed unnecessary.

A representative sample of the embodiment of FIGS. 8 and 9 having a width of 6.5 mm, a thickness of 7.5 mm, a radius for each circular section of 3.5 mm, a groove or notch depth for each laterally opening groove of 2.75 mm and a thickness adjacent laterally opening grooves of 2.0 mm results in each segment having a 4.7% increase in surface area.

Figure 10:
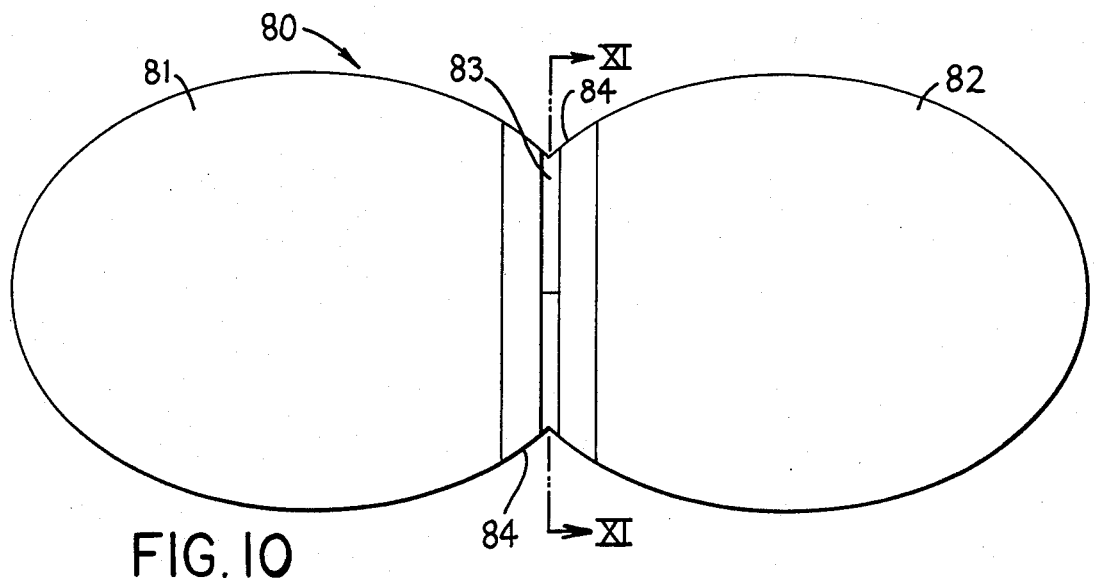
FIG. 10 is the top view of a divisible tablet having a still further different shape.
Figure 11:
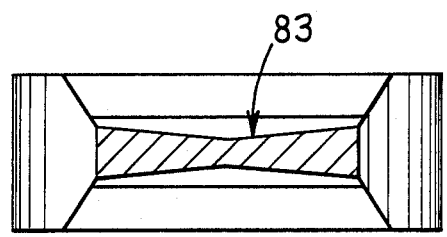
FIG. 11 is a sectional view taken along the line XI—XI of FIG. 10.

An elliptical bidosage tablet 80 is illustrated in FIGS. 10 and 11. In this particular embodiment, the tablet 80 is comprised of two tablet sections 81 and 82 which are elliptical in shape. The common edge 83 is identical to the common edge structure described, for example, in the embodiments of FIGS. 1 to 5. Thus, further detailed description about the common edge construction 83 is believed unnecessary. The tablet 80 has a pair of laterally opening notches 84 on opposite lateral sides thereof which are comparable to the notches 55 illustrated in the embodiment of FIGS. 6 and 7.

Assuming a tablet segment length of three times the height or thickness, a tablet width that is equal to the height and a total top and bottom groove depth equal to two fifths of the tablet height, an elliptical bidosage tablet, such as is illustrated in FIGS. 10 and 11, will result in the formation of only 3.0% new surface on each half when the whole tablet is divided into two halves.

In an effort to determine a range of desirable low percentage of new surface area following a severing of a divisible tablet into its severed parts, several examples were reviewed and constructed. The several examples were each guided by the accepted dimension criteria for the largest of such divisible tablets which is still swallowable in its entirety, namely, each tablet (caplet) shall have a size that is no greater than one inch (25.4 mm) in length by one half inch (12.7 mm) in width or, if circular, no greater than 12.7 mm in overall diameter. Each divisible tablet is to have a mass of 1 gram or less. Tablets substantially outside the aforementioned dimension criteria are not within the scope of the present invention as these tablets will not be easily swallowable.

The following examples represent other differently shaped divisible tablets reviewed. Note that the shape of the new surface area is rectangular or circular. The preferred shape of the new surface area is as is shown in FIGS. 2, 4, 7 and 9 because it is believed stronger even though the new surface area is comparable to the new surface area in the following examples.

EXAMPLE 1

CIRCULAR BIDOSAGE TABLET (with rectangular new surface)

|  | Tablet Dimensions For Maximum Increase in Surface Area | Tablet Dimensions For Experimental Tablet |
|---|---|---|
| Width: | 12.7 mm | 9.7 mm |
| Thickness: | 7.5 mm | 5.0 mm |
| Depth of laterally extending groove: | 1.0 mm | — |
| Depth of laterally opening groove: | 2.0 mm | — |
| Length of laterally extending groove: | — | 6.0 mm |
| Thickness at laterally extending groove: | — | 2.0 mm |
| Whole Tablet Surface Area: | 1105 sq mm | 600 sq mm |
| Total New Surface Area: | 95.7 sq mm | 24.0 sq mm |
| % Increase in Surface Area Upon Division: | 8.66% | 4.00% |

EXAMPLE 2

CIRCULAR TRIDOSAGE TABLET (with rectangular new surface)

|  | Tablet Dimensions For Maximum Increase in Surface Area | Tablet Dimensions For Representative Tablet |
|---|---|---|
| Width: | 6.5 mm | 6.5 mm |
| Thickness: | 7.5 mm | 7.5 mm |
| Radius of each circular section | 3.5 mm | 3.5 mm |
| Depth of laterally extending groove: | 2.25 mm | 2.75 mm |
| Thickness at laterally extending groove: | 3.0 mm | 2.0 mm |
| Whole Tablet Surface Area: | 495 sq mm | 495 sq mm |
| Total New Surface Area: | 69.2 sq mm | 46.1 sq mm |
| % Increase in Surface Area Upon Division: | 13.98% | 9.32% |

EXAMPLE 3

ELLIPTICAL BIDOSAGE TABLETS (with circular new surface)

|  | Tablet Dimensions For Maximum Increase in Surface Area | Tablet Dimensions For Representative Tablet |
|---|---|---|
| Length: | 15.0 mm | 15.0 mm |
| Diameter and Width: | 6.35 mm | 6.35 mm |
| Groove Depth: | 1.0 mm | 1.425 mm |
| Length of Center Section: | 4.0 mm | 4.0 mm |
| Whole Tablet Surface Area: | 294 sq mm | 327 sq mm |
| Total New Surface Area: | 29.7 sq mm | 19.2 sq mm |
| % Increase in Surface Area Upon Division: | 10.1% | 5.88% |

EXAMPLE 4

ELLIPTICAL BIDOSAGE TABLET (with rectangular new surface)

|  | Tablet Dimensions For Maximum Increase in Surface Area | Tablet Dimensions For Representative Tablet |
|---|---|---|
| Length: | 15.0 mm | 15.0 mm |
| Diameter and Width: | 6.35 mm | 6.35 mm |
| Depth of laterally extending groove: | 1.0 mm | 1.5 mm |
| Depth of laterally opening groove: | 1.0 mm | 1.5 mm |
| Whole Tablet Surface Area: | 299 sq mm | 299 sq mm |
| Total New Surface Area: | 37.9 sq mm | 22.5 sq mm |
| % Increase in Surface Area Upon Division: | 12.7% | 7.50% |

In view of the four examples set forth above, it is apparent that the range of total new surface area is between 4.00% and 13.98% of the total surface area of the separated parts of the tablet.

Although particular preferred embodiments of the invention have been described in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A divisible matrix tablet, divisible into tablet segments, with or without coating, having controlled and delayed release of an active substance, comprising breakable connecting means in the form of laterally extending grooves on the top and bottom tablet surfaces directly opposite each other at each line of division; and at least one laterally opening groove on one side of the tablet at least at one end of said laterally extending grooves thereby making the length of said laterally extending grooves less than a width dimension of a tablet segment when measured along a line parallel to said laterally extending grooves, and means in at least one of said laterally extending grooves for effecting a reduction in a newly formed surface area created when said first and second body parts are severed along said laterally extending grooves, so that said newly formed surface area is less than 15% of the total surface area of said separated first or second body parts.

2. The divisible matrix tablet according to claim 1, wherein said laterally extending grooves and laterally opening grooves define a cylindrically shaped breakable connecting means.

3. The divisible matrix tablet according to claim 1, wherein the depth of said laterally extending grooves varies along its length, being greatest at the geometric center of said grooves and achieving a minimum depth at the ends of said grooves.

4. The divisible matrix tablet according to claim 1, wherein the depth of said laterally extending grooves varies along its length, being greatest at one end of said grooves and achieving a minimum depth at the other end of said groove.

5. The divisible matrix tablet construction according to claim 1, wherein the maximum mass of said divisible matrix tablet is one gram.

6. The tablet according to claim 1, wherein each of said grooves is V-shaped in cross section, the bottom of each groove extending along the length of said groove in a straight line.

7. The tablet according to claim 1, wherein said tablet consists only of said first and second body parts.

8. The tablet according to claim 1, wherein said tablet consists only of three body parts, any tow body parts constituting said first and second body parts.

9. The tablet according to claim 1, wherein each of said grooves is V-shaped in cross section, the bottom of each groove extending along the length of said groove in straight lines intersecting at said geometric center.

10. A divisible matrix tablet, with or without coating, having controlled and delayed release of an active substance, comprising;
first and second body parts, each having top and bottom facing surfaces joined together at a perimeter by an edge means;
breakable connecting means for joining together said first and second body parts at a perimeter portion thereof, said breakable connecting means being formed by depressions in said top and bottom facing surfaces of said perimeter portion of said first and second body parts, each said depression being directly opposite the other and having first and second score surfaces facing each other, the depth of each said depression varying along the length of said breakable connecting means, the depth of each said depression being the greatest at the geometric center of said breakable connecting means tapering to minimum depth at the ends of said breakable connecting means.

11. The divisible matrix tablet according to claim 10, wherein said edge means at both of said ends of said breakable connecting means is provided with means defining a recess to thereby make the length of said breakable connecting means less than a maximum width dimension of said first and second body parts measured along a line parallel to said breakable connecting means.

12. The divisible matrix tablet according to claim 11, wherein said depth of each said depression tapers to no depth at the ends of said breakable connecting means.

13. The divisible matrix tablet according to claim 12, wherein the location of said no depth portion of said depression is directly at one end of said breakable connecting means.

14. The divisible matrix tablet according to claim 10, wherein the width of each said depression between said first and second score surfaces is uniform along the length of said breakable connecting means.

15. The divisible matrix tablet according to claim 10, wherein the maximum mass of said divisible matrix tablet is one gram.

16. The tablet according to claim 1, wherein each depression is defined by a groove a groove V-shaped in cross section, the bottom of each groove extending along the length of said groove in straight lines intersecting at said geometric center.

17. The tablet according to claim 1, wherein said tablet consists only of said first and second body parts.

18. The tablet according to claim 1, wherein said tablet consists only of three body parts, any two body parts constituting said first and second body parts.

19. The tablet according to claim 1, wherein a newly formed surface area created when said first and second body parts are severed along said breakable connecting means is less than 15% of the total surface area of said separated first or second body parts.

20. The tablet according to claim 1, wherein said edge means at least at one end of said breakable connecting means is provided with means defining a recess to thereby make the length of said breakable connecting means less than a maximum width dimension of said first and second body parts measured along a line parallel to said breakable connecting means.

21. A divisible matrix tablet, with or without coating, having controlled and delayed release of an active substance, comprising;
first and second body parts, each having top and bottom facing surfaces joined together at a perimeter by an edge means;
breakable connecting means for joining together said first and second body parts at a perimeter portion thereof, said breakable connecting means being formed by depressions in said top and bottom facing surfaces of said perimeter portion of said first and second body parts, each said depression being directly opposite the other and having first and second score surfaces facing each other, the depth of each said depression varying along the length of said breakable connecting means, the depth of each said depression being the greatest at one end of said breakable connecting means tapering to a minimum depth at the other end of said breakable connecting means.

22. The divisible matrix tablet according to claim 21, wherein the location of said greatest depth of said depression is directly at one end of said breakable connecting means.

23. The divisible matrix tablet according to claim 21, wherein the maximum mass of said divisible matrix tablet is one gram.

24. The tablet according to claim 21, wherein each depression is defined by a groove V-shaped in cross section, the bottom of each groove extending along the length of said groove in a straight line.

25. The tablet according to claim 21, wherein said tablet consists only of said first and second body parts.

26. The tablet according to claim 21, wherein said tablet consists only of three body parts, any two body parts constituting said first and second body parts.

27. The tablet according to claim 21, wherein a newly formed surface area created when said first and second body parts are severed along said breakable connecting means is less than 15% of the total surface area of said separated first or second body parts.

28. The tablet according to claim 21, wherein said edge means at least at one end of said breakable connecting means is provided with means defining a recess to thereby make the length of said breakable connecting means less than a maximum width dimension of said first and second body parts measured along a line parallel to said breakable connecting means.

* * * * *

UNITED STATES PATENT AND TRADEMARK OFFICE
CERTIFICATE OF CORRECTION

PATENT NO. : 4 824 677
DATED : April 25, 1989
INVENTOR(S) : Ashok C. SHAH et al.

It is certified that error appears in the above-identified patent and that said Letters Patent is hereby corrected as shown below:

Title page:

In the Abstract: line 1; change "table" to ---tablet---.
line 5; change "of" to ---by---.
Column 4; line 25; change "63" to ---64---.
line 45; after "adjacent" insert ---the---.
Column 7; line 17; delete "construction".
line 27; change "tow" to ---two---.
Column 8; line 7; delete "a groove" (second occurrence).

Signed and Sealed this

Fifteenth Day of May, 1990

Attest:

HARRY F. MANBECK, JR.

*Attesting Officer*     *Commissioner of Patents and Trademarks*